(12) United States Patent
Rangabhatla Gunneswara Subramanya

(10) Patent No.: US 11,533,929 B2
(45) Date of Patent: Dec. 27, 2022

(54) GREEN TEA FILM COMPOSITION

(71) Applicant: SHILPA MEDICARE LIMITED, Raichur (IN)

(72) Inventor: Vara Prasad Rangabhatla Gunneswara Subramanya, Bangalore (IN)

(73) Assignee: Shilpa Medicare Limited ( * ) Notice: Subject to any disclaimer, the term of this patent is extended or adjusted under 35 U.S.C. 154(b) by 0 days.

(21) Appl. No.: 16/635,163

(22) PCT Filed: Dec. 23, 2019

(86) PCT No.: PCT/IB2019/061263
§ 371 (c)(1),
(2) Date: Jan. 29, 2020

(87) PCT Pub. No.: WO2020/141404
PCT Pub. Date: Jul. 9, 2020

(65) Prior Publication Data
US 2021/0315228 A1    Oct. 14, 2021

(30) Foreign Application Priority Data
Jan. 5, 2019 (IN) .............................. 201941000551

(51) Int. Cl.
| A23F 3/30 | (2006.01) |
| A23L 29/262 | (2016.01) |
| A23L 33/105 | (2016.01) |
| A23L 29/256 | (2016.01) |
| A23L 29/288 | (2016.01) |
| A23L 2/395 | (2006.01) |
| A23L 2/56 | (2006.01) |
| A23L 2/60 | (2006.01) |
| A61K 9/70 | (2006.01) |
| A61K 36/82 | (2006.01) |
| A61K 47/36 | (2006.01) |
| A61K 47/38 | (2006.01) |

(52) U.S. Cl.
CPC ................ *A23F 3/30* (2013.01); *A23L 2/395* (2013.01); *A23L 2/56* (2013.01); *A23L 2/60* (2013.01); *A23L 29/256* (2016.08); *A23L 29/262* (2016.08); *A23L 29/288* (2016.08); *A23L 33/105* (2016.08); *A61K 9/7007* (2013.01); *A61K 36/82* (2013.01); *A61K 47/36* (2013.01); *A61K 47/38* (2013.01); *A23V 2002/00* (2013.01)

(58) Field of Classification Search
CPC ........ A23F 3/30; A23L 29/262; A23L 33/105; A23L 2/395; A23L 2/60; A61K 9/707; A61K 36/82; A61K 47/36; A61K 47/38; A23V 2002/00
USPC ......................................... 426/597, 575, 573
See application file for complete search history.

(56) References Cited

FOREIGN PATENT DOCUMENTS

| CA | 2545961 | * | 5/2021 |
| WO | 2015088221 A1 | | 6/2015 |

OTHER PUBLICATIONS

Han et al. 2016 "Sodium alginate/carboxymethyl cellulose films containing pyrogallic acid", pp. 1-17. www.researchgate.net/publication/304325515_Sodium_alginatecarboxymethyl-cell_. (Year: 2 016).*
Science Direct abstracts, p. 1, "Carbomers", 2016, and p. 4, paragraph 15.3.3.1 (Carbomers), www.sciencedirect.com/topics/medicine-and-dentistry/carbomer. 2018 pp. 1-9 (Year: 2020).*

* cited by examiner

Primary Examiner — Helen F Heggestad

(57) ABSTRACT

The present invention relates to novel green tea water soluble film composition comprising a) green tea extract, b) water soluble polymer mixture consisting of sodium carboxymethyl cellulose and sodium alginate, and c) additives. Green tea is conveniently prepared by dissolving the novel water soluble green tea film of the said invention in hot water.

6 Claims, No Drawings

GREEN TEA FILM COMPOSITION

FIELD OF INVENTION

The present invention relates to a novel green tea film preparation comprising a water soluble polymer and green tea extract as an effective ingredient, specifically a water soluble green tea film for green tea preparation by dissolving green tea film with a water soluble polymer to drink simply and conveniently by dissolving in hot water, and the method for preparation thereof.

BACKGROUND OF THE INVENTION

Green tea herb has been used for preparing green tea for many years, since it contains various ingredients for good health, for example inorganic ingredients, vitamins, anti-oxidants or anti-bacterial components as functional ingredients.

Recently various green tea type products such as dried green tea leaf itself, granule type green tea, disposable green tea bag, have been developed and marketed conventionally.

Generally, the conventionally marketed green tea products have various disadvantages, for example inconvenience to clean the un-used green tea leaf or disposable green tea bag soaked in remaining water, which cause difficulty in handling and cleaning. Moreover, such disposable tea bag may burst and give rise to other disadvantages, for example, difficulty in controlling proper brewing time to obtain most palatable taste.

In order to overcome the above disadvantages of green tea leaf or disposable green tea bag, inventors of PCT Publication No. WO2015/088221 have developed a water soluble film type herb tea preparation comprising a water soluble polymer, an herb extract and a plasticizer. The inventors of WO '221 Publication have developed a green tea film comprising a water soluble polymer selected from pullulan or pectin and mixtures thereof comprising of about 2% w/w to about 40% w/w of total composition of the film. The films as disclosed in WO '221 patent are brittle, fragile in nature and have bitter taste. Therefore, there exists a need to develop the water soluble film comprising green tea extract, and a water soluble polymer that have better film forming properties, faster disintegration time and pleasant taste.

The inventors of the present invention have intensively investigated to improve the film formation and disintegration time of water soluble film comprising green tea extract, as a result of investigation, the inventors have surprisingly discovered a novel water soluble film composition comprising green tea extract and water soluble polymer mixture consisting of sodium carboxymethyl cellulose and sodium alginate that have the advantages of better film forming properties, faster disintegration time, flexibility, pleasant taste and faster disintegration rate etc.

SUMMARY OF THE INVENTION

The present invention relates to a water soluble film composition comprising green tea extract and water soluble polymer mixture consisting of sodium carboxymethyl cellulose and sodium alginate.

The present invention further relates to a water soluble film composition comprising green tea extract and water soluble polymer mixture consisting of sodium carboxymethyl cellulose, sodium alginate and cross-linked polyacrylate polymer.

The present invention further relates to a water soluble film composition comprising
a) green tea extract,
b) water soluble polymer mixture consisting of sodium carboxymethyl cellulose and sodium alginate, and
c) additives.

The present invention further relates to a water soluble film composition comprising
a) green tea extract,
b) water soluble polymer mixture consisting of sodium carboxymethyl cellulose, sodium alginate and cross-linked polyacrylate polymer, and
c) additives.

The present invention also relates to a water soluble film composition comprising
a) green tea extract,
b) water soluble polymer mixture consisting of sodium carboxymethyl cellulose and sodium alginate, and
c) additives;
wherein the ratio of sodium carboxymethyl cellulose and sodium alginate in the composition is between 1:2 and 1:5.

The present invention further relates to a water soluble film composition comprising
a) green tea extract,
b) water soluble polymer mixture consisting of sodium carboxymethyl cellulose, sodium alginate and cross-linked polyacrylate polymer, and
c) additives;
wherein the ratio of sodium carboxymethyl cellulose and sodium alginate in the composition is between 1:2 and 1:5.

The present invention also relates to a water soluble film composition comprising
a) green tea extract,
b) water soluble polymer mixture consisting of about 2% w/w to about 5% w/w of sodium carboxymethyl cellulose and of about 15% w/w to about 25% w/w sodium alginate based on the total weight of the film, and
c) additives.

The present invention also relates to a water soluble film composition comprising
a) green tea extract,
b) water soluble polymer mixture consisting of about 2% w/w to about 5% w/w of sodium carboxymethyl cellulose; about 15% w/w to about 25% w/w sodium alginate and about 0.5% w/w to about 5% w/w cross-linked polyacrylate polymer based on the total weight of the film, and
c) additives.

The present invention further relates to a water soluble film composition comprising
a) green tea extract,
b) water soluble polymer mixture consisting of about 2% w/w to about 5% w/w of sodium carboxymethyl cellulose and of about 15% w/w to about 25% w/w sodium alginate based on the total weight of the film, and
c) at least one additive selected from plasticizers, diluents, sweetening agents, disintegrating agents, colouring agents and flavoring agents.

The present invention also relates to a water soluble film composition comprising
a) green tea extract,
b) water soluble polymer mixture consisting of about 2% w/w to about 5% w/w of sodium carboxymethyl cellulose; about 15% w/w to about 25% w/w sodium alginate; about 0.5% w/w to about 5% w/w cross-linked polyacrylate polymer based on the total weight of the film, and c) at least one additive selected from plasticizers, diluents, sweetening agents, disintegrating agents, colouring agents and flavoring agents.

DETAILED DESCRIPTION OF THE INVENTION

The present invention provides a water soluble film composition comprising green tea extract and water soluble polymer mixture consisting of sodium carboxymethyl cellulose and sodium alginate.

The present invention further relates to a water soluble film composition comprising green tea extract and water soluble polymer mixture consisting of sodium carboxymethyl cellulose, sodium alginate and cross-linked polyacrylate polymer (Carbopol®).

As used herein in connection with numerical values, the terms "about" mean +/−5% of the indicated value, including the indicated value.

The term "green tea extract" defined herein comprises all conventionally available material which is used to make green tea. The water soluble film composition of the present invention comprises of about 40% w/w to about 60% w/w of green tea extract, based on the total weight of the film, preferably from about 45% w/w to about 55% w/w based on the total weight of the film, more preferably from about 48% w/w to about 53% w/w based on the total weight of the film and most preferably about 49% w/w based on the total weight of the film.

The water soluble polymer mixture used in the present invention is mixture of polymers selected from the group consisting of sodium carboxymethyl cellulose and sodium alginate.

In the embodiments of the present invention, the water soluble polymer mixture used in the present invention is a mixture of sodium carboxymethyl cellulose and sodium alginate, wherein the ratio of sodium carboxymethyl cellulose and sodium alginate in the composition is between 1:2 and 1:5.

In a further embodiment water soluble polymer mixture used in the present invention is mixture of polymers selected from the group consisting of sodium carboxymethyl cellulose, sodium alginate and cross-linked polyacrylate polymer In embodiments of the invention the water soluble film composition of the present invention comprises of about 0.01% w/w to about 10% w/w of sodium carboxymethyl cellulose, based on the total weight of the film, preferably from about 1% w/w to about 8% w/w based on the total weight of the film, more preferably from about 2% w/w to about 5% w/w based on the total weight of the film and most preferably about 4% w/w based on the total weight of the film composition.

In embodiments of the invention the water soluble film composition of the present invention comprises of about 5% w/w to about 40% w/w of sodium alginate, based on the total weight of the film, preferably from about 10% w/w to about 30% w/w based on the total weight of the film, more preferably from about 15% w/w to about 25% w/w based on the total weight of the film and most preferably about 21% w/w based on the total weight of the film composition.

In embodiments of the invention the water soluble film composition of the present invention comprises of about 0.1% w/w to about 10% w/w of cross-linked polyacrylate polymer based on the total weight of the film, preferably from about 0.5% w/w to about 5% w/w based on the total weight of the film, more preferably from about 0.5% w/w to about 2% w/w based on the total weight of the film composition.

In embodiments of the present invention, the invention provides a water soluble film composition comprising a) green tea extract,
b) water soluble polymer mixture consisting of sodium carboxymethyl cellulose and sodium alginate, and
c) additives.

In another embodiment, the present invention provides a water soluble film composition comprising a) green tea extract,
b) water soluble polymer mixture consisting of sodium carboxymethyl cellulose, sodium alginate and cross-linked polyacrylate polymer, and
c) additives.

In a further embodiment, the present invention provides a water soluble film composition comprising a) green tea extract,
b) water soluble polymer mixture consisting of sodium carboxymethyl cellulose and sodium alginate, and
c) additives;
wherein the ratio of sodium carboxymethyl cellulose and sodium alginate in the composition is between 1:2 and 1:5.

In embodiment of the invention, the present invention provides a water soluble film composition comprising a) green tea extract,
b) water soluble polymer mixture consisting of sodium carboxymethyl cellulose, sodium alginate and cross-linked polyacrylate polymer, and
c) additives;
wherein the ratio of sodium carboxymethyl cellulose and sodium alginate in the composition is between 1:2 and 1:5.

In embodiment of the invention, the present invention provides a water soluble film composition comprising a) green tea extract,
b) water soluble polymer mixture consisting of about 2% w/w to about 5% w/w of sodium carboxymethyl cellulose and of about 15% w/w to about 25% w/w sodium alginate based on the total weight of the film, and
c) additives.

In further embodiment of the invention, the present invention provides a water soluble film composition comprising a) green tea extract,
b) water soluble polymer mixture consisting of about 2% w/w to about 5% w/w of sodium carboxymethyl cellulose; about 15% w/w to about 25% w/w sodium alginate and about 0.5% w/w to about 5% w/w cross-linked polyacrylate polymer based on the total weight of the film, and
c) additives.

In another embodiment of the invention the present invention provides a water soluble film composition comprising a) green tea extract,
b) water soluble polymer mixture consisting of about 2% w/w to about 5% w/w of sodium carboxymethyl cellulose and of about 15% w/w to about 25% w/w sodium alginate based on the total weight of the film, and
c) at least one additive selected from plasticizers, diluents, sweetening agents, disintegrating agents, colouring agents and flavoring agents.

In another embodiment of the invention, the present invention provides a water soluble film composition comprising
  a) green tea extract,
  b) water soluble polymer mixture consisting of about 2% w/w to about 5% w/w of sodium carboxymethyl cellulose; about 15% w/w to about 25% w/w sodium alginate; about 0.5% w/w to about 5% w/w cross-linked polyacrylate polymer based on the total weight of the film, and
  c) at least one additive selected from plasticizers, diluents, sweetening agents, disintegrating agents, colouring agents and flavoring agents.

In further embodiment, the present invention provides a water soluble film composition comprising
  a) of about 48% w/w to about 53% of green tea extract,
  b) water soluble polymer mixture consisting of about 2% w/w to about 5% w/w of sodium carboxymethyl cellulose and of about 15% w/w to about 25% w/w sodium alginate based on the total weight of the film, and
  c) additives.

In still further embodiment, the present invention provides a water soluble film composition comprising
  a) of about 49% w/w of green tea extract,
  b) water soluble polymer mixture consisting of about 4% w/w of sodium carboxymethyl cellulose and of about 21% w/w sodium alginate based on the total weight of the film, and
  c) additives.

In embodiments of the invention, the present invention provides a water soluble film composition comprising
  a) of about 48% w/w to about 53% green tea extract,
  b) water soluble polymer mixture consisting of about 2% w/w to about 5% w/w of sodium carboxymethyl cellulose and of about 15% w/w to about 25% w/w sodium alginate based on the total weight of the film, and
  c) at least one additive selected from plasticizers, diluents, sweetening agents, disintegrating agents, colouring agents and flavoring agents.

In still further embodiment, the present invention provides a water soluble film composition comprising
  a) of about 49% w/w of green tea extract,
  b) water soluble polymer mixture consisting of about 4% w/w of sodium carboxymethyl cellulose and of about 21% w/w sodium alginate based on the total weight of the film, and
  c) at least one additive selected from plasticizers, diluents, sweetening agents, disintegrating agents, colouring agents and flavoring agents.

In further embodiment, the present invention provides a water soluble film composition comprising
  a) of about 45% w/w to about 55% of green tea extract,
  b) water soluble polymer mixture consisting of about 2% w/w to about 5% w/w of sodium carboxymethyl cellulose; about 15% w/w to about 25% w/w sodium alginate and about 0.5% w/w to about 5% w/w cross-linked polyacrylate polymer based on the total weight of the film, and
  c) additives.

The term "plasticizer" defined herein comprises all the conventionally available material which can control the flexibility of the film and the plasticizers are selected from group consisting of glycerol, propylene glycol, polyethylene glycol, triacetin and acetyl citrate. The plasticizer preferably used in the present inventive composition is glycerol which is present in the range from about 1% w/w to about 20% w/w, more preferably in the range of about 2% w/w to about 18% w/w, even more preferably in the range of about 2% w/w to about 8% w/w and most preferably of about 5% w/w based on the total weight of film composition.

Suitable diluents that can be included are mannitol, microcrystalline cellulose (for example, microcrystalline cellulose available under the trade mark Avicel), silicified microcrystalline cellulose, starches or modified starches (including potato starch, corn starch, maize starch and rice starch), tribasic calcium phosphate and magnesium aluminometasilicate. The most preferred diluent used in the present composition is magnesium aluminometasilicate which is present in the range of about 0.5% w/w to about 10% w/w, more preferably in the range of about 0.5% w/w to about 10% w/w and most preferably in the range of about 1% w/w to about 5% w/w based on the total weight of the film composition.

Suitable sweetening agents that can be included are those well known in the art, selected from group consisting of sorbitol, xylose, ribose, glucose (dextrose), mannose, galactose, fructose (levulose), sucrose (sugar), maltose, invert sugar (a mixture of fructose and glucose derived from sucrose), steviosides, and glycyrrhizin. The sweetening agent preferably used in the present composition is sorbitol which is present in the range from about 5% w/w to about 20% w/w, more preferably in the range of about 7% w/w to about 15% w/w and most preferably of about 11% w/w based on the total weight of film composition.

Suitable disintegrating agents for the preparation of the film according to the present invention is hydroxypropyl pea starch (hydroxypropyl starch), pregelatinized starch, croscarmellose sodium and sodium starch glycolate. The disintegrating agent preferably used in the present composition is hydroxypropyl pea starch which is present in the range from about 0.1% w/w to about 10% w/w, more preferably in the range of about 2% w/w to about 7% w/w and most preferably of about 4% w/w based on the total weight of film composition.

The flavouring agents that can be used include those known to the skilled artisan, such as natural and artificial flavors. These flavouring agents may be chosen from synthetic flavor oils and flavoring aromatics, and/or oils, oleo resins and extracts derived from plants, leaves, flowers, fruits and so forth, and combinations thereof. Representative flavour oil include: spearmint oil, lemon oil, ginger oil, cinnamon oil, peppermint oil, clove oil, bay oil, thyme oil, cedar leaf oil, oil of nutmeg, oil of sage, and oil of bitter almonds. Representative flavour from leaves include green tea leaf extract flavour. Also useful are artificial, natural or synthetic fruit flavors such as vanilla, banana, chocolate, coffee, cocoa and citrus oil, including lemon, orange, grape, lime and grapefruit and fruit essences including apple, pear, peach, strawberry, raspberry, cherry, plum, pineapple, apricot and so forth. These flavourings can be used individually or in admixture. Commonly used flavors include mints such as peppermint, artificial vanilla, cinnamon derivatives, and various fruit flavors, whether employed individually or in admixture. Flavorings such as aldehydes and esters including cinnamyl acetate, cinnamaldehyde, citral, diethylacetal, dihydrocarvyl acetate, eugenyl formate, p-methylanisole, and so forth may also be used. Generally, any flavoring or food additive, such as those described in Chemicals Used in Food Processing, publication 1274 by the National Academy of Sciences, pages 63 258, may be used. Further examples of aldehyde flavourings include, but are not limited to acetaldehyde (apple); benzaldehyde (cherry, almond); cinnamic aldehyde (cinnamon); citral, i.e., alpha citral (lemon, lime); neral, i.e. beta citral (lemon, lime); decanal (orange, lemon); ethyl vanillin (vanilla, cream); heliotropine, i.e., piperonal (vanilla, cream); vanillin (vanilla, cream); alpha-amyl cinnamaldehyde (spicy fruity flavors); butyraldehyde (butter, cheese); valeraldehyde (butter, cheese); citronellal (modifies, many types); decanal (citrus fruits); aldehyde C-8 (citrus fruits); aldehyde C-9 (citrus fruits); aldehyde C-12 (citrus fruits); 2-ethyl butyraldehyde (berry fruits); hexenal, i.e. trans-2 (berry fruits); tolyl aldehyde (cherry, almond); veratraldehyde (vanilla); 2,6-dimethyl-5-heptenal, i.e. melonal (melon); 2-6-dimethyloctanal (green fruit); and 2-dodecenal (citrus, mandarin); cherry; grape; honey or mixtures thereof; and the like.

The colouring agents useful in the present invention include pigments such as titanium dioxide, which may be incorporated in amounts of up to about 5 wt %, and preferably less than about 1 wt %. Colouring agents can also include natural food colors and dyes suitable for food, drug and cosmetic applications. These colouring agents are known as FD&C dyes and lakes. The materials acceptable for the foregoing spectrum of use are preferably water-soluble, and include Carmosine, FD&C Blue No. 2, which is the disodium salt of 5,5-indigotindisulfonic acid. Similarly, the dye known as Green No. 3 comprises a triphenyl-methane dye and is the monosodium salt of 4-[4-N-ethyl-p-sulfobenzylamino) diphenyl-methylene]-[1-N-ethyl-N-p-sulfonium benzyl)-2,5-cyclo-hexadienimine]. A full recitation of all FD&C and D&C dyes and their corresponding chemical structures may be found in the Kirk-Othmer Encyclopedia of Chemical Technology, Volume 5, Pages 857-884, which text is accordingly incorporated herein by reference.

In further embodiments of the invention, the present invention provides a water soluble film composition comprising
a) of about 48% w/w to about 53% green tea extract,
b) water soluble polymer mixture consisting of about 2% w/w to about 5% w/w of sodium carboxymethyl cellulose and of about 15% w/w to about 25% w/w sodium alginate based on the total weight of the film,
c) of about 2% w/w to about 8% w/w of plasticizers,
d) of about 7% w/w to about 15% w/w of sweetening agents,
e) of about 2% w/w to about 7% w/w disintegrating agents, and
f) flavouring agents.

In another embodiments of the invention, the present invention provides a water soluble film composition consisting of
a) about 48% w/w to about 53% green tea extract,
b) water soluble polymer mixture consisting of about 2% w/w to about 5% w/w of sodium carboxymethyl cellulose and of about 15% w/w to about 25% w/w sodium alginate based on the total weight of the film,
c) about 2% w/w to about 8% w/w of plasticizers,
d) about 7% w/w to about 15% w/w of sweetening agents,
e) about 2% w/w to about 7% w/w disintegrating agents, and
f) flavouring agents.

In still further embodiment, the present invention provides a water soluble film composition comprising of
a) about 49% w/w of green tea extract,
b) water soluble polymer mixture consisting of about 4% w/w of sodium carboxymethyl cellulose and of about 21% w/w sodium alginate based on the total weight of the film and
c) about 5% w/w of glycerol,
d) about 11% w/w of sorbitol,
e) about 4% w/w of hydroxypropyl pea starch, and
f) flavouring agents.

In still further embodiment, the present invention provides a water soluble film composition consisting of
a) about 49% w/w of green tea extract,
b) water soluble polymer mixture consisting of about 4% w/w of sodium carboxymethyl cellulose and of about 21% w/w sodium alginate based on the total weight of the film and
c) about 5% w/w of glycerol,
d) about 11% w/w of sorbitol,
e) about 4% w/w of hydroxypropyl pea starch, and
f) flavouring agents.

In another embodiment, the present invention relates to provide a method of preparing a water soluble film composition comprising
a) green tea extract,
b) water soluble polymer mixture consisting of about 2% w/w to about 5% w/w of sodium carboxymethyl cellulose and of about 15% w/w to about 25% w/w sodium alginate based on the total weight of the film, and
c) additives.

In embodiment, the present invention relates to provide a method of preparing a water soluble film composition comprising the steps of
a) mixing of about 4% w/w of sodium carboxymethyl cellulose solution with about 4% w/w of hydroxypropyl pea starch,
b) adding of about 21% w/w of sodium alginate with contents of step a,
c) adding of about 49% w/w of green tea extract to contents of step b,
d) adding ginger oil, lemon oil, peppermint flavour to contents of step c,
e) adding glycerol to contents of step d,
f) adding the sorbitol to contents of step e, and
g) obtaining the film composition on polyester film.

In further embodiments of the invention, the present invention provides a water soluble film composition comprising
a) about 45% w/w to about 55% green tea extract,
b) water soluble polymer mixture consisting of about 2% w/w to about 5% w/w of sodium carboxymethyl cellulose; of about 15% w/w to about 25% w/w sodium alginate and about 0.5% w/w to about 5% w/w cross-linked polyacrylate polymer based on the total weight of the film,
c) about 1% w/w to about 5% w/w diluents,
d) about 2% w/w to about 18% of plasticizers,
e) about 2% w/w to about 7% w/w disintegrating agents, and
f) flavouring agents.

In further embodiments of the invention, the present invention provides a water soluble film composition consisting of
a) about 45% w/w to about 55% green tea extract,
b) water soluble polymer mixture consisting of about 2% w/w to about 5% w/w of sodium carboxymethyl cellulose; of about 15% w/w to about 25% w/w sodium alginate and about 0.5% w/w to about 5% w/w cross-linked polyacrylate polymer based on the total weight of the film,
c) about 1% w/w to about 5% w/w diluents,
d) about 2% w/w to about 18% w/w of plasticizers,
e) about 2% w/w to about 7% w/w disintegrating agents, and
f) flavouring agents.

The following examples are provided to illustrate the present invention. It is understood, however, that the invention is not limited to the specific conditions or details described in the examples below. The examples should not be construed as limiting the invention as the examples merely provide specific methodology useful in the understanding and practice of the invention and its various aspects. While certain preferred and alternative embodiments of the invention have been set forth for purposes of disclosing the invention, modification to the disclosed embodiments can occur to those who are skilled in the art.

Example 1

Composition:

| S. No | Component | mg/Strip | (% w/w) |
|---|---|---|---|
| 1 | Green tea extract | 120 | 49.3% |
| 2 | Glycerol | 12 | 4.9% |
| 3 | Sodium carboxymethyl cellulose | 10 | 4.1% |
| 4 | Sodium alginate | 50 | 20.6% |
| 5 | Hydroxypropyl pea starch | 10 | 4.1% |
| 6 | Sorbitol | 28 | 11.5% |
| 7 | Green Tea flavor | 10 | 4.1% |
| 8 | Nova Mint (Peppermint) | 0.5 | 0.2% |
| 9 | Lemon Oil | 2.0 | 0.8% |
| 10 | Ginger Oil | 1.0 | 0.4% |
| | Total | 243.5 | 100% |

Process for Preparation:
1. Preparation of Sodium Alginate Base solution: Weighed quantity of purified water was taken in a beaker and slowly Sodium Alginate powder was added to it under continuous stirring, and the stirring was continued until sodium alginate disperses uniformly and kept aside for overnight for removal/escape of air bubbles.
2. Preparation of Sodium carboxymethyl cellulose dispersion: Weighed quantity of purified water was taken in a beaker and Sodium carboxymethyl cellulose (Cekol 200P) was added to it and sonicated it for 15 minutes and kept aside for 8 hrs for uniform dispersion of sodium carboxymethyl cellulose in the water.
3. Slurry Preparation:
   i. Weighed quantity of sodium carboxymethyl cellulose solution was taken from step 2 in beaker.
   ii. Weighed quantity of pregelatinized hydroxy propyl pea starch (Lycoat RS 780) was added to step No. i and stirred it for 2-3 minutes.
   iii. Weighed quantity of Sodium Alginate base was added to step No. ii and stirred for 6-8 minutes.
   iv. Weighed quantity of Green tea extract was added to step No. iii and stirred for 8-10 minutes.
   v. Weighed quantity of Green tea flavor was added to step No. iv and stirred it for 2-4 minutes.
   vi. Weighed quantity of Ginger oil was added to step No. v and stirred it for 6-8 minutes.
   vii. Weighed quantity of Lemon oil was added to step No. vi and stirred it for 6-8 minutes.
   viii. Weighed quantity of Peppermint (Nova type) was added to step No. vii and stirred it for 2-4 minutes.
   ix. Weighed quantity of Glycerol was added to step No. viii and stirred for 6-8 minutes.
   x. Weighed quantity of Sorbitol Liquid was added to step No. ix and stirred for 8-10 minutes and then kept aside for removal/escape air bubbles to from green tea extract slurry.
4. Layering & Drying: The above green tea extract slurry was layered on polyester film and dried at 90° C. for 18 min.
5. Slitting & Packing: The above dried film was slit into required size (32×32 mm & 32×40 mm) and packed in to primary packing material (Triple Laminate).

Example 2

Composition:

| S. No | Component | mg/Strip | (% w/w) |
|---|---|---|---|
| 1 | Green tea extract | 120 | 49.5% |
| 2 | Glycerol | 12 | 4.9% |
| 3 | Sodium carboxymethyl cellulose | 10 | 4.1% |
| 4 | Sodium alginate | 45 | 18.6% |
| 5 | Hydroxypropyl pea starch | 10 | 4.1% |
| 6 | Sorbitol | 32 | 13.2% |
| 7 | Green Tea flavor | 10 | 4.1% |
| 8 | Nova Mint (Peppermint) | 0.5 | 0.2% |
| 9 | Lemon Oil | 2.0 | 0.8% |
| 10 | Ginger Oil | 1.0 | 0.4% |
| | Total | 243.5 | |

The composition is prepared by the process as disclosed in Example 1.

Example 3

Composition:

| S. No | Component | mg/Strip | (% w/w) |
|---|---|---|---|
| 1 | Green tea extract | 120 | 56.5% |
| 2 | Glycerol | 12 | 5.6% |
| 3 | Sodium carboxymethyl cellulose | 10 | 4.7% |
| 4 | Sodium alginate | 15 | 7.1% |
| 5 | Hydroxypropyl pea starch | 10 | 4.7% |
| 6 | Sorbitol | 32 | 15% |
| 7 | Green Tea flavor | 10 | 4.7% |
| 8 | Nova Mint (Peppermint) | 0.5 | 0.2% |
| 9 | Lemon Oil | 2.0 | 0.9% |
| 10 | Ginger Oil | 1.0 | 0.5% |
| | Total | 212.5 | |

The composition is prepared by the process as disclosed in Example 1.

Example 4

Composition:

| S. No | Component | mg/Strip | (% w/w) |
|---|---|---|---|
| 1 | Green tea extract | 120 | 46.51% |
| 2 | Glycerol | 39 | 15.1% |
| 3 | Sodium carboxymethyl cellulose | 10 | 3.87% |
| 4 | Sodium alginate | 50 | 19.37% |
| 5 | Cross-linked polyacrylate polymer | 1.50 | 0.58% |
| 6 | Magnesium Alumino silicate | 5 | 1.93% |
| 7 | Hydroxypropyl pea starch | 18 | 6.97% |
| 8 | Green Tea flavor | 11 | 4.26% |
| 9 | Peppermint (Nova) Mint | 0.5 | 0.19% |
| 10 | Lemon Oil | 2.0 | 0.77% |
| 11 | Ginger Oil | 1.0 | 0.38% |
| | Total | 258.0 | |

The process for preparation of Example 4 is analogous to Example 1, wherein Magnesium alumino silicate is added instead of sorbitol and Cross-linked polyacrylate polymer is added slurry preparation step 3.

Comparative Example 1 & 2

| S. No | Component | Comparative Example 1 mg/Strip | Comparative Example 1 % w/w | Comparative Example 2 mg/Strip | Comparative Example 2 % w/w |
|---|---|---|---|---|---|
| 1 | Green tea extract | 120 | 49.3% | 120 | 49.3% |
| 2 | Glycerol | 10 | 4.1% | 10 | 4.1% |
| 3 | Pullulan | 60 | 24.6% | 96 | 39.4% |
| 4 | Hydroxypropyl pea starch | 9 | 3.7% | 5 | 2.1% |
| 5 | Sorbitol | 31 | 12.7% | — | — |
| 6 | Green Tea flavor | 10 | 4.1% | 9 | 3.7% |
| 7 | Nova Mint | 0.5 | 0.2% | 0.5 | 0.2% |
| 8 | Lemon Oil | 2.0 | 0.8% | 2 | 0.8% |
| 9 | Ginger Oil | 1.0 | 0.4% | 1 | 0.4% |
|  | Total | 243.5 | 100% | 243.5 | 100% |

The process for preparation of Example 4 is analogous to Example 1, wherein Pullulan is used as a polymer in step 3 as polymer.

Example 4

Physical Property Test on the Inventive Film

In order to evaluate the physical property on inventive green tea film, the physical property was performed by 5 panelists on the film shape, flexibility and dissolution rate. The result was shown in Table 1 and the high score means the better shaped film.

The criteria for determining the film shape was by observation and scored to 3 grades i.e., 2 points (well-structured), 1 point (unstably-structured) and 0 points (broken structure).

The criteria for determining the film flexibility was by confirming the degree of shape failure when the film was forced to bend by hand and scored to 3 grades i.e., 2 points (no failure when the film was bend to 180° angle); 1 point (failure when the film was bend more than 90° angle) and 0 points (failure when the film was bended less than 90° angle).

The criteria for determining the disintegrating rate of inventive film by confirming the disintegrating rate where the film was dipped in to water at 90° C. was scored for 3 grades, i.e 2 points (dissolved in less than 30 seconds), 1 point (dissolve within 30 seconds and 1 minute) and 0 point (dissolved in above 1 minute).

As shown in table 1, the film having 20.6% w/w of sodium alginate and 4.1% w/w of sodium carboxymethyl cellulose (example 1) showed better physical property to film shape, flexibility and disintegration rate. Further the film as disclosed in example 4 also showed better physical property to film shape, flexibility and disintegration rate.

TABLE 1

| Example No. | Film Shape | Flexibility | Disintegration rate | Physical Property (Total Points 30) |
|---|---|---|---|---|
| Example 1 | 10 | 9 | 10 | 29 |
| Example 2 | 8 | 8 | 10 | 26 |
| Example 3 | 4 | 6 | 8 | 18 |
| Example 4 | 10 | 10 | 9 | 29 |
| Comparative Example 1 | 4 | 4 | 6 | 14 |
| Comparative Example 2 | 4 | 4 | 4 | 12 |

I claim:

1. A water soluble film composition consisting essentially of a) about 40% w/w to about 60% w/w green tea extract, b) water soluble polymer mixture consisting of about 2% w/w to about 5% w/w sodium carboxymethyl cellulose and about 15% w/w to about 25% w/w sodium alginate, and c) additives.

2. The water soluble film composition according to claim 1, wherein the additives are selected from plasticizers, diluents, sweetening agents, disintegrating agents, colouring agents and flavoring agents.

3. A water soluble film composition consisting essentially of a) about 40% w/w to about 60% w/w green tea extract, b) water soluble polymer mixture consisting of about 2% w/w to about 5% w/w sodium carboxymethyl cellulose, about 15% w/w to about 25% w/w sodium alginate and about 0.5% w/w to about 5% w/w cross-linked polyacrylate polymer, and c) additives.

4. The water soluble film composition according to claim 3, wherein the additives are selected from plasticizers, diluents, sweetening agents, disintegrating agents, colouring agents and flavoring agents.

5. A water soluble film composition consisting of
a) about 40% w/w to about 60% green tea extract,
b) water soluble polymer mixture consisting of about 2% w/w to about 5% w/w of sodium carboxymethyl cellulose and of about 15% w/w to about 25% w/w sodium alginate based on the total weight of the film,
c) about 2% w/w to about 8% w/w of plasticizers,
d) about 7% w/w to about 15% w/w of sweetening agents,
e) about 2% w/w to about 7% w/w disintegrating agents, and
f) flavouring agents.

6. A water soluble film composition consisting of
a) about 40% w/w to about 60% w/w green tea extract,
b) water soluble polymer mixture consisting of about 2% w/w to about 5% w/w of sodium carboxymethyl cellulose; of about 15% w/w to about 25% w/w sodium alginate and about 0.5% w/w to about 5% w/w cross-linked polyacrylate polymer based on the total weight of the film,
c) about 1% w/w to about 5% w/w diluents,
d) about 2% w/w to about 18% of plasticizers,
e) about 2% w/w to about 7% w/w disintegrating agents, and
f) flavouring agents.

* * * * *